(12) United States Patent
Bassi et al.

(10) Patent No.: US 8,376,956 B2
(45) Date of Patent: Feb. 19, 2013

(54) DEVICE AND METHOD FOR DETERMINING A CAP ARRANGEMENT INDICATING COLOR DISCRIMINATION

(75) Inventors: Carl J. Bassi, St. Louis, MO (US); Michael Howe, St. Charles, MO (US); Wayne Garver, St. Louis, MO (US)

(73) Assignee: The Curators of the University of Missouri, Columbia, MO (US)

( * ) Notice: Subject to any disclaimer, the term of this patent is extended or adjusted under 35 U.S.C. 154(b) by 277 days.

(21) Appl. No.: 12/522,691

(22) PCT Filed: Jan. 8, 2008

(86) PCT No.: PCT/US2008/050502
§ 371 (c)(1),
(2), (4) Date: Nov. 24, 2009

(87) PCT Pub. No.: WO2008/086346
PCT Pub. Date: Jul. 17, 2008

(65) Prior Publication Data
US 2010/0125221 A1 May 20, 2010

Related U.S. Application Data

(60) Provisional application No. 60/884,117, filed on Jan. 9, 2007.

(51) Int. Cl.
*A61B 5/00* (2006.01)
(52) U.S. Cl. .................................................. 600/558
(58) Field of Classification Search .................. 600/558
See application file for complete search history.

(56) References Cited

U.S. PATENT DOCUMENTS

| | | | |
|---|---|---|---|
| 5,796,250 A * | 8/1998 | Dames | 324/207.22 |
| 5,938,620 A * | 8/1999 | Daxer | 600/558 |
| 7,157,715 B1 | 1/2007 | Crain, Jr. et al. | |
| 2004/0043443 A1 * | 3/2004 | Lejeune | 435/29 |
| 2005/0046502 A1 | 3/2005 | Singh et al. | |
| 2005/0084243 A1 | 4/2005 | Higurashi | |

* cited by examiner

*Primary Examiner* — Max Hindenburg
(74) *Attorney, Agent, or Firm* — Senniger Powers LLP

(57) ABSTRACT

A detector located on a positioning tray has a plurality of colored caps placed by a subject being tested. Each cap has a unique resonant circuit which is selectively energized to indicate cap position to the detector so that color discrimination of the subject may be determined.

20 Claims, 9 Drawing Sheets

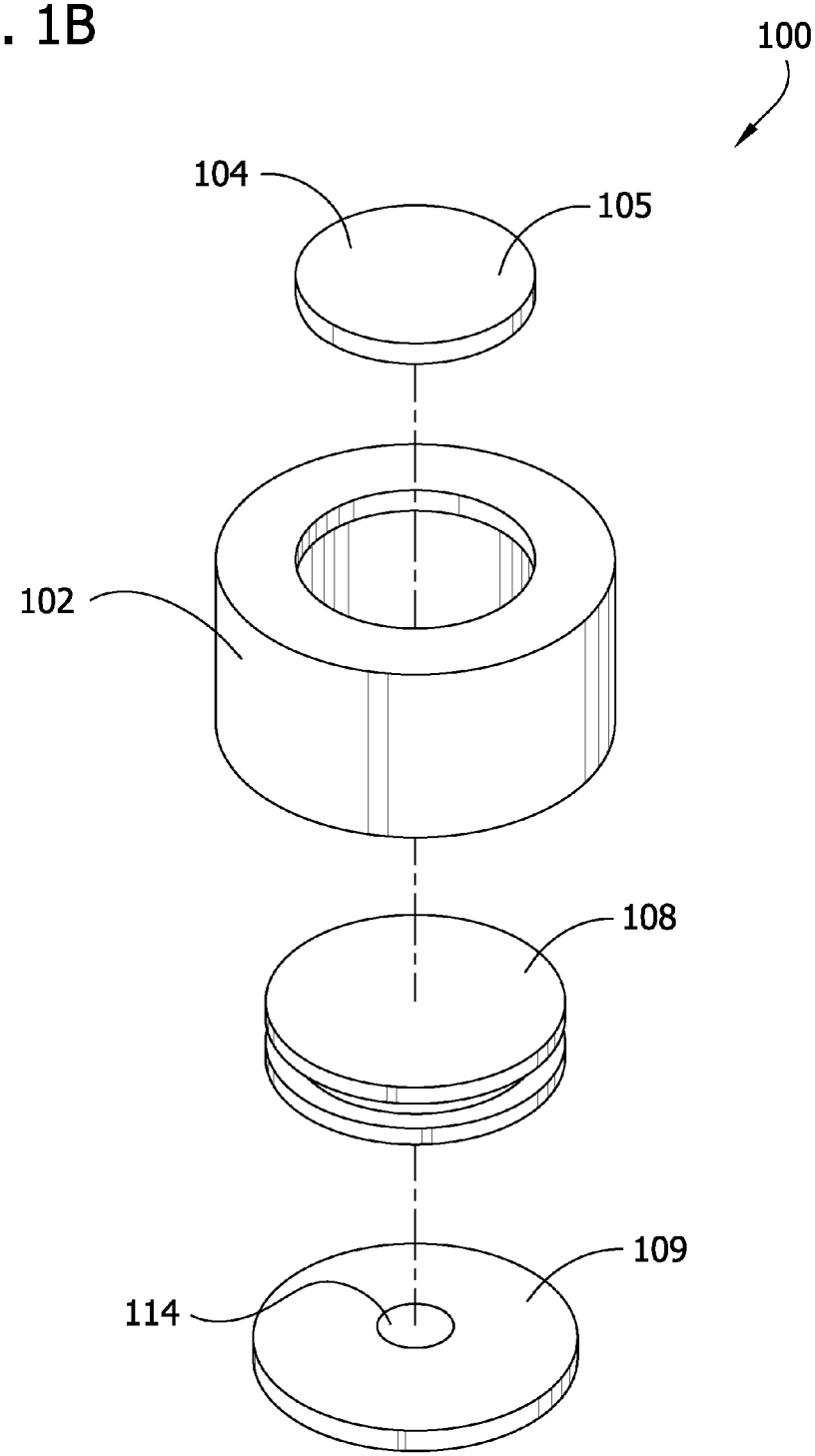

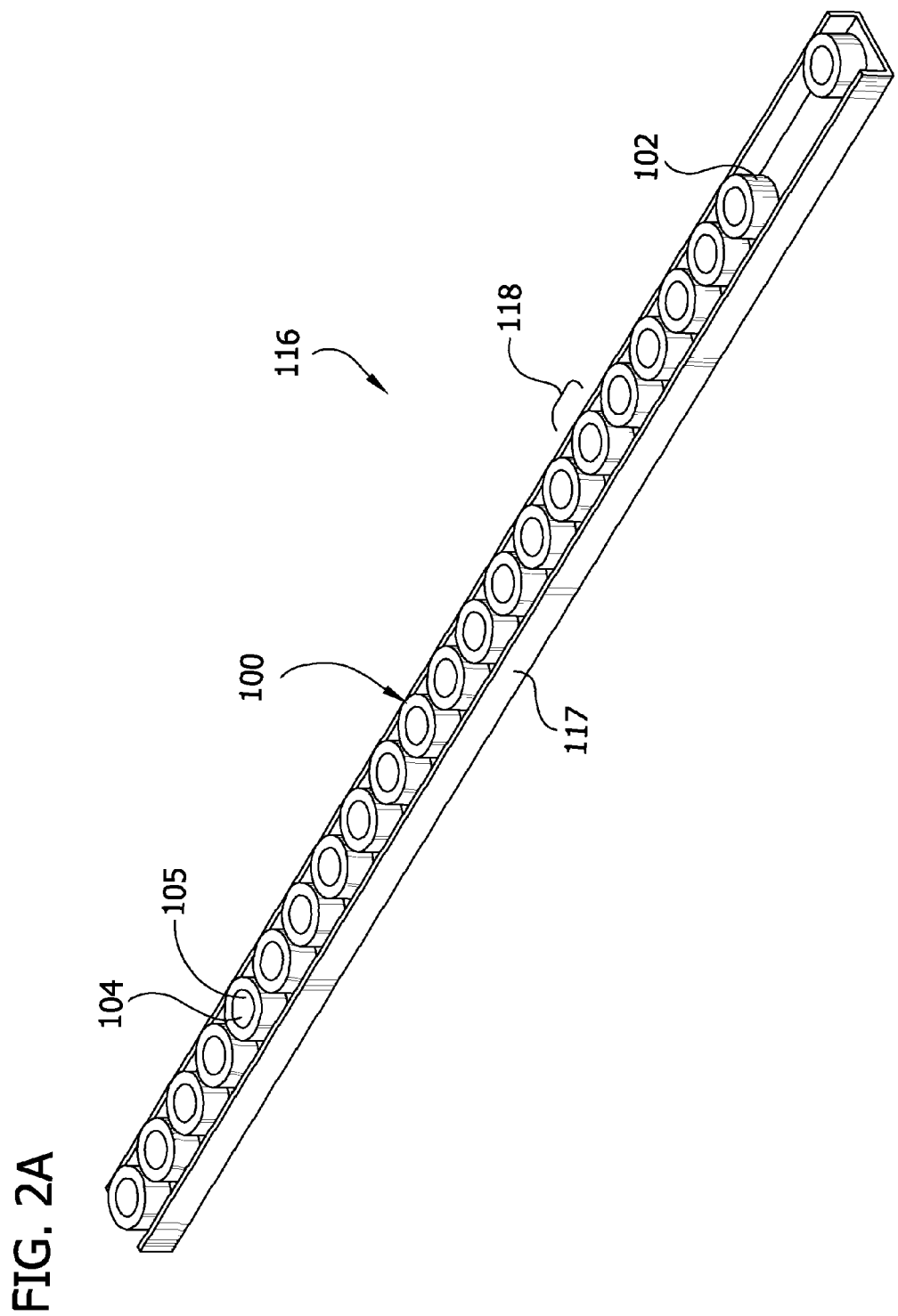

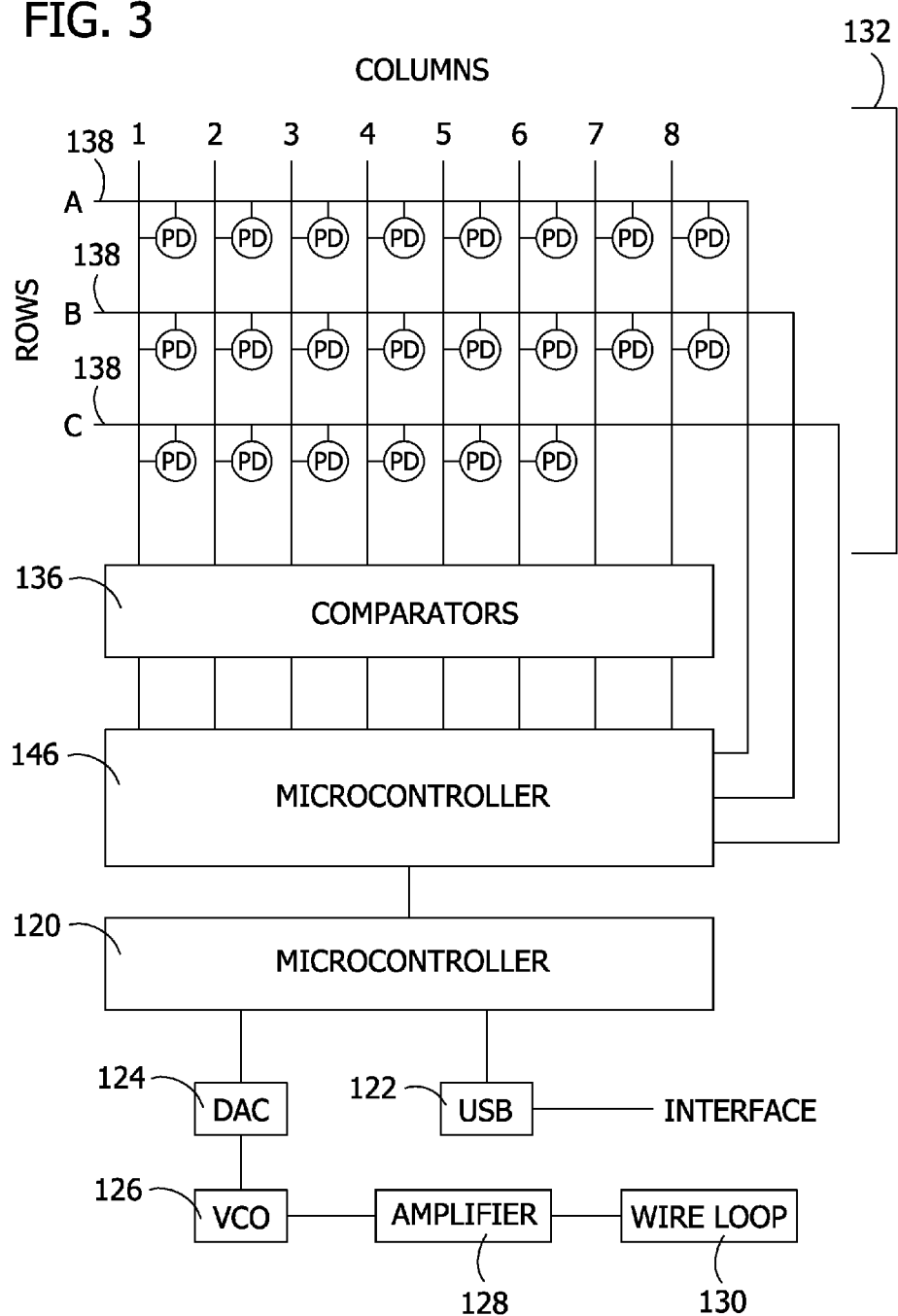

DEVICE AND METHOD FOR DETERMINING A CAP ARRANGEMENT INDICATING COLOR DISCRIMINATION

FIELD OF THE INVENTION

The present invention generally relates to a device for determining the color discrimination of a subject, and more particularly, a device for automatically detecting the sequence of caps of differing hues used in administering arrangement tests.

BACKGROUND OF THE INVENTION

One way to define poor color vision is the inability to discriminate between different hues. There are different varieties and degrees of poor color vision. The "normal" human retina contains three cone photoreceptors termed the long wavelength sensitive, middle wavelength sensitive, and short wavelength sensitive cones. Protan deficiencies refer to either a loss or an abnormal absorption of the long wavelength sensitive cones, deutan deficiencies refer to either a loss or an abnormal absorption of the middle wavelength sensitive cones, and Tritan deficiencies refer to either a loss or an abnormal absorption of the short wavelength sensitive cones. The incidence of protan and deutan deficiencies are common in congenital color problems and the incidence of tritan and more diffuse deficiencies are more common with acquired color deficiencies. Poor color vision is a relatively common problem for many subjects. Clinical estimates suggest the number of subjects having a congenital color vision in the population is nearly 8% for males and 1% for females. The incidence is much higher if all of the other known causes of color deficiencies such as diseases, side-effects of some medications, trauma, aging, and exposure to certain chemicals or other environmental factors are included. Poor color vision is generally undesirable because many jobs and everyday activities requires average or superior color discrimination.

Several tests for determining color discrimination are widely used. These tests are broadly categorized into pseudo-isochromatic plates, arrangement tests, matching tests, and naming tests. Arrangement tests are generally considered reliable and are frequently used by practioners. In arrangement tests, subjects sequentially arrange, according to perceived color proximity, a number of loose caps that vary in hue. Three well-known arrangement tests are the Farnsworth Munsell D-15, the L'Anthony desaturated D-15, and the Farnsworth Munsell 100 hue test.

The Farnsworth Munsell 100 hue test is designed to detect all types of color vision abnormalities. Additionally, the test can separate subjects with normal color vision into classes of superior, average and low color discrimination and detect and measure the zones of color confusion. The test uses 85 movable and 8 fixed caps, each with a diameter of 21 mm. These 93 caps, each having a color spot, form a sample of the natural color spectrum and of the range of purple colors. The caps are distributed among four trays. When placed one abutting the other using the criterion that the most similar colors are arranged one after the other, the caps produce a closed color circle. Each cap, and hence each color spot, is assigned a number which makes it possible to calculate how many partial mistakes are made and to calculate the total number of errors. The pattern and total number of errors are parameters used to monitor the type and severity of color vision disorders.

There are two important reliability issues associated with the implementation and scoring process of the three cap arrangement tests. The first issue relates to the transferring of the subject's arrangement into a particular scoring sheet. Conventionally, the tester does this by lifting the caps arranged by the subject, flipping them upside down, reading the number on the underside of the cap, and transcribing the number in the particular scoring sheet. This process is time-consuming and involves a certain likelihood of error resulting in inaccurate reports. The second issue relates to the data analysis conducted on the discrepancies between the subject-arranged cap arrangement and the correct color order. Where this scoring is performed manually is it time consuming, extending up to an hour.

Currently there are several computer-based methods that expedite the scoring calculations and interpretation of test results. However, these methods still require the arranged caps to be manually lifted and flipped upside down and manually entered into the program for analysis. To eliminate these shortcomings, an automatic transcription of the subject's arrangements to the host computer is needed.

U.S. Pat. No. 5,938,620 attempts to fulfill these objectives with an apparatus including a positioning tray, a plurality of color caps movably located in the positioning tray, and a series of fixed magnets located on the bottom of each of the color caps. Each cap has a unique arrangement of magnets. A series of magnetic detectors in the tray identify the strength and arrangement of the magnets. An evaluation unit analyzes the cap order and the information is then transmitted for further evaluation to a computer system. This invention requires one detector for each magnet located on the bottom of each cap. The number of magnets needed per cap depends on the number of caps used for the testing. Because several detectors are needed per cap in order to administer the arrangement tests discussed above, the resulting invention can be quite costly. Another shortcoming of this invention relates to the detection accuracy. A particular cap must be oriented so the magnets located on the cap align with the detectors corresponding to each cap in the positioning tray to ensure an accurate detection of the particular cap. Additionally, there is a certain likelihood of cross-talk between the caps and detectors when the caps are in certain arrangements. A further shortcoming involves the cost and monitoring required to replace or recalibrate the invention because the magnets have lost strength over the course of time or have been dropped or otherwise damaged in the normal course of testing. Thus, there remains a need for a device for determining color discrimination of a subject by automatically detecting the sequence of caps which is efficient, reliable, robust, and relatively inexpensive.

SUMMARY OF THE INVENTION

Embodiments of the invention overcome one or more deficiencies of current practices related to determining color discrimination by using caps having unique circuits and a positioning tray having an energizing circuit to selectively energize the circuits of each of the caps placed in the positioning tray. Each unique circuit is detected when energized and the position in the positioning tray of each cap having the energized circuit is recorded. In addition, embodiments of the invention advantageously use only one detector for detecting the position of each cap and accurately detect the position of each cap despite the planar rotational orientation of the cap in the positioning tray.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Other objects and features will be in part apparent and in part pointed out hereinafter.

BRIEF DESCRIPTION OF THE DRAWINGS

FIG. 1B is an exploded view of a cap illustrating a combination and placement of internal components according to one embodiment of the invention.

FIG. 2A is a front perspective view illustrating a positioning tray with a plurality of caps arranged therein according to one embodiment of the invention.

FIG. 3 is a block diagram illustrating a photodetector matrix and related components according to one embodiment of the invention.

Corresponding reference characters indicate corresponding parts throughout the drawings.

DETAIL DESCRIPTION

Figure 1A:
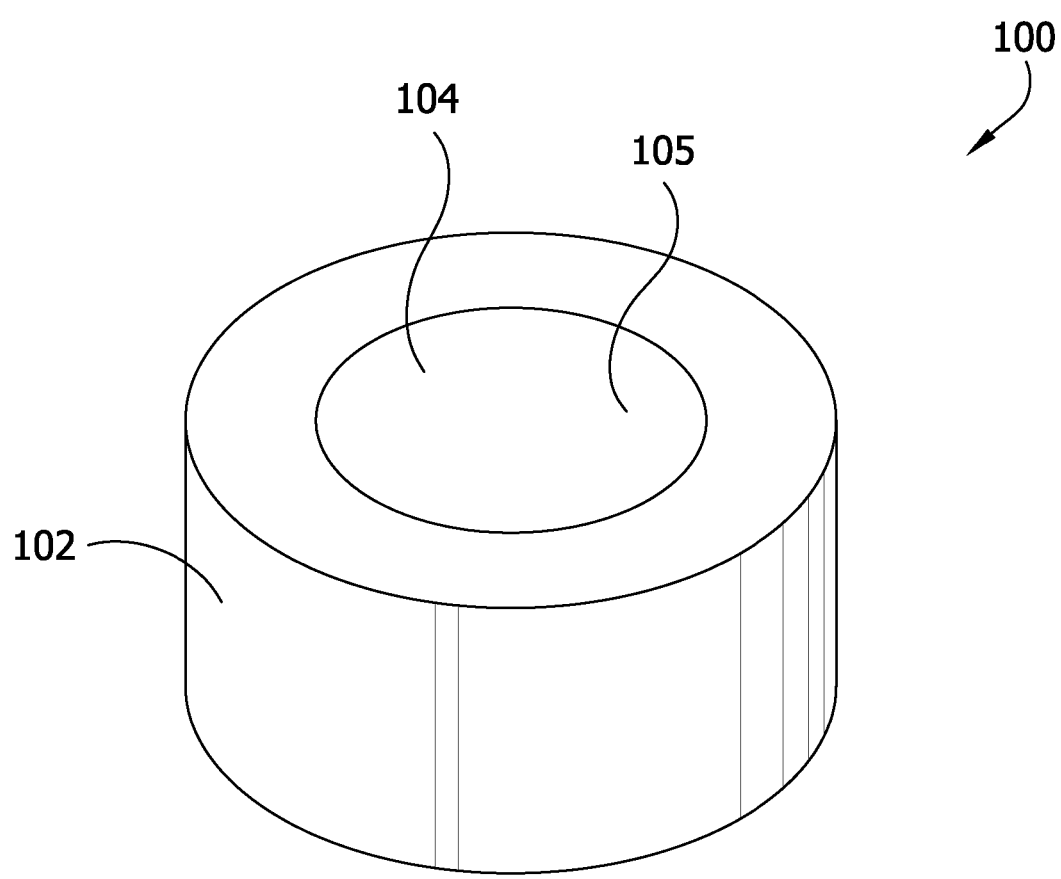
FIG. 1A is a top perspective view of a cap according to one embodiment of the invention.

Referring first to FIGS. 1A, 1B, 1C, 2A, and 2B, one embodiment of a device comprising a plurality of caps, generally indicated 100, and a positioning tray, generally indicated 116, for determining color discrimination of a subject is depicted. When the subject undergoes color discrimination testing, a plurality of loose caps 100 are provided, each cap 100 displaying a color 104, for positioning in the positioning tray 116 by the subject. The positioning tray 116 has a plurality of positions 118, each position 118 for receiving one of the plurality of caps 100. The subject is instructed to arrange the plurality of caps 100 in the positioning tray 116 in a particular order based on the color displayed 104 by each of the caps 100. In the arrangement tests discussed above, each of the plurality of caps 100 displays a different color 104 or hue in a range of the natural color spectrum. The subject is asked to arrange the caps 100 in the positioning tray 116 according to the subject's perceived color proximity of the color displayed by the caps 100. Caps with similar colors are positioned adjacent each other so that the colors displayed by the caps range from one color to another. Accordingly, the subject arranges the plurality of caps 100 in the positioning tray 116 by placing one cap 100 in each position 118 of the positioning tray 116. The color discrimination of the subject can then be determined by comparing the positions 118 in the positioning tray 116 of each of the caps 100 to a standard arrangement. One standard arrangement is the caps 100 correctly arranged according to color proximity of the color displayed 104 by each cap 100.

The positions 118 in the positioning tray 116 of each of the plurality of caps 100 as placed by the subject are determined. Each particular cap 100 has a unique circuit 108 which is unique to the particular cap and which is associated with the color of each cap 104. The unique circuit 108 of each of the plurality of caps 100 emits a signal when energized by an energizing circuit 130 included in the positioning tray 116. A separate detector 133 is located on the positioning tray 116 at each position 118 to detect the signal emitted by the unique circuit 108 at each position 118 when the circuit is energized and emits a detection signal. A controller 120 is connected to the detectors 133 for recording the detected position 118 of each energized cap 100.

In operation, the energizing circuit 130 in the positioning tray 116 is selectively energized to sequentially energize each of the unique circuits 108, one at a time. When the circuit 108 of a particular cap 100 is energized, the circuit 108 emits a signal detected by the detector 133 at the position 118 at which the particular cap is located. The detector 133 emits a signal indicating the position 118 of particular cap 100 which is provided to the controller 120 so that the controller 120 records the position 118 of the cap. This method is repeated in order to selectively, sequentially energize each of the unique circuits 108 associated with the colors 104 displayed by each cap 100 to detect the position of each cap 118 displaying the selected color 104. Thus, the positions 118 in the positioning tray 116 of each of the plurality of caps 100, as arranged by the subject according to color, are determined.

FIGS. 1A and 1B generally depict the components of the cap. As illustrated in FIG. 1A, the cap 100 includes a protective outer housing 102 and a colored cylindrical disc indicator 105 adhered to the protective outer housing 102. The outer housing 102 protects the unique circuit 108 and displays the indicator 105. The indicator 105 is viewed by the subject and compared to the indicators 105 of the other caps 100 when the caps 100 are initially given to the subject for testing and while the subject arranges the caps 100 in the positioning tray 116. The outer housing 102 and the indicator 105 may take on different forms and locations known in the art with respect to each other. For example, the indicator 105 may be integrated into the outer housing 102 by coloring the material comprising the outer housing 102 of the cap 100 (e.g., where the outer housing 102 is comprised of plastic, the plastic would be of the color 104). Alternatively, the indicator 105 may be completely enclosed in the outer housing 102 wherein the outer housing 102 is translucent or otherwise displays the color 104 to the subject (e.g., the outer housing could be comprised of a translucent plastic and the colored cylindrical disc indicator could be adhered to the underside of the top surface of the outer housing 102 so that the color of the disc indicator would be visible through the housing 102). Additionally, the outer housing 102 and the indicator 105 shown in FIG. 1A are cylindrically shaped because the rotational symmetry provides for ease in operation, as explained below. However, other geometric shapes could be used for both the outer housing 102 and the indicator 105.

As illustrated in FIG. 1B, the cap 100 further includes the unique circuit 108 and a circuit board 109. As depicted, both the unique circuit 108 and the circuit board 109 are partially housed inside the protective outer housing 102 leaving an opening 107 through which the signal emitted by the unique circuit 108 can be transmitted to the detector 133 located on the positioning tray 116. However, the unique circuit 108 and circuit 109 can take on other forms and locations with respect to the outer housing 102 without departing from the scope of the invention. For example, the circuit board 109 and unique circuit 108 could be adhered to an outer surface of the outer housing 102 or the outer housing 102 could serve as the circuit board 109 by having traces in to which the circuit components are directly mounted. Additionally, both the unique circuit 108 and the circuit board 109 could be completely enclosed within outer housing 102 or partially housed leaving various sizes and shapes of openings 107.

Figure 1C:
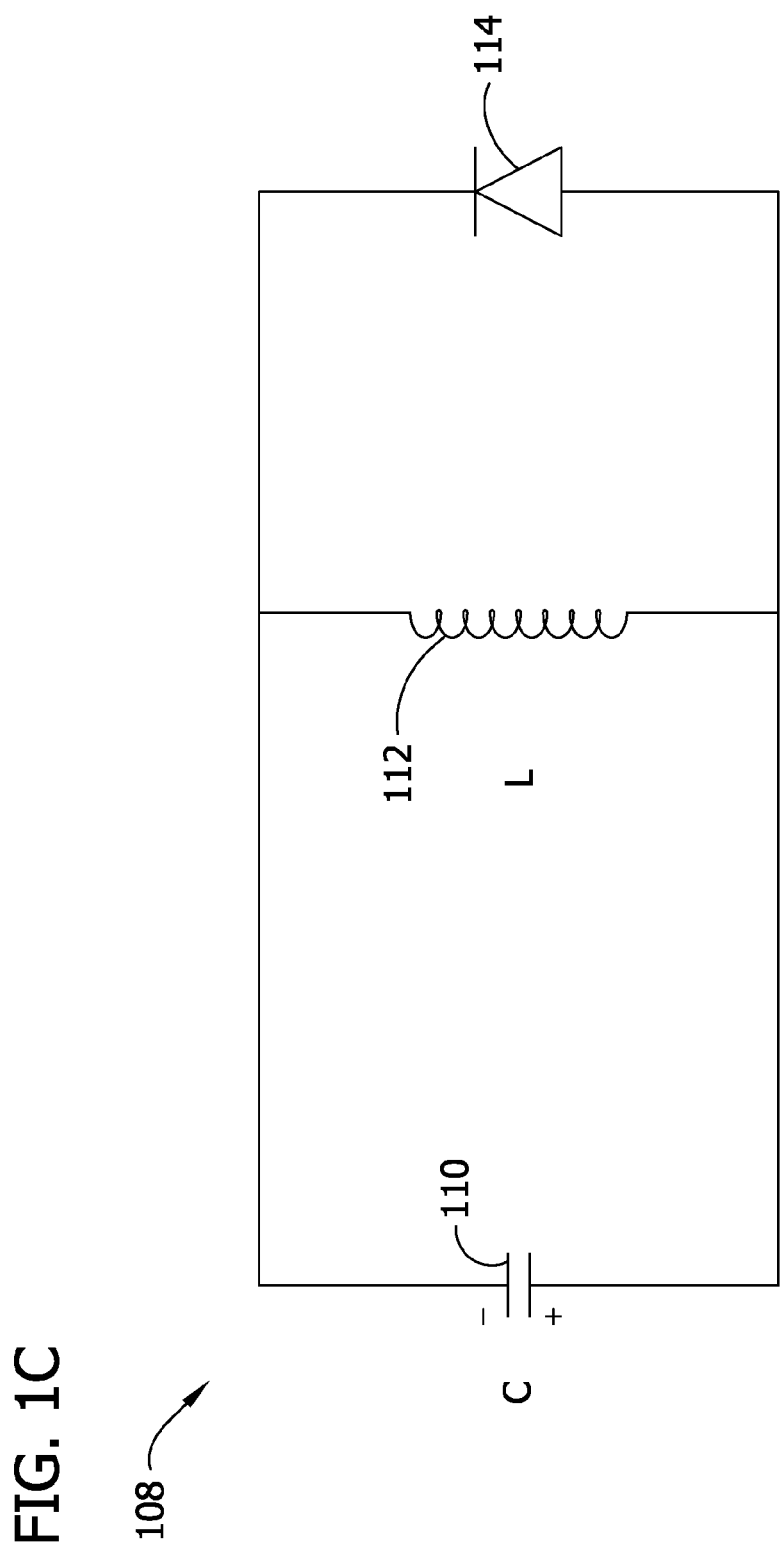
FIG. 1C is a circuit schematic of the internal components of the cap according to the embodiment illustrated in FIG. 1B.

In one embodiment, the unique circuit 108 of each of the plurality of caps 100 is a passive resonant circuit 108, depicted by FIG. 1C, having a unique resonant frequency at which the passive resonant circuit 108 is energized. Each cap having a unique resonant frequency means that there is only a narrow range of frequencies at which each particular cap will resonate, determined by components comprising the resonant circuit and their relationship to each other, and said one specific frequency is different as compared to the frequencies of all other caps. The unique resonant frequency is known and associated with the color displayed 104 by the cap having the passive resonant circuit 108 with said unique resonant frequency. The resonant circuit 108 is passive in that it does not include a power source because the resonant circuit 108 is energized by the energizing circuit 130 in the positioning tray 116. In operation, the energizing circuit 130 in the positioning tray 116 generates a particular resonant frequency associated with a cap 100 displaying a particular color 104. Accordingly, the passive resonant circuit 108 of the cap 100 displaying the particular color 104 is energized emitting a signal used to determine the position 118 in the positioning tray 116 of the cap 100 displaying the particular color 104.

In the particular embodiment illustrated in FIG. 1C, the passive resonant circuit 108 of each of the plurality of caps 100 comprises a capacitance (C) 110, an inductance (L) 112, and a light emitting diode (LED) 114 electrically connected in parallel. The resonant circuit 108 has a resonant frequency f according to the following relationship:

$$f = \frac{1}{2\pi\sqrt{LC}}$$

where L is measured in henries, C is measured in Farads, and f is measured in hertz. In one embodiment, the passive resonant circuit 108 of each of the plurality of caps 100 is designed to have a unique resonant frequency by using a value for inductance 112 which is substantially the same for each of the caps 100 and by using a value for capacitance 110 that is different for each of the plurality of caps 100. When a circuit is energized by circuit 130 at the unique resonant frequency, the circuit 108 energizes the LED 114 to emit light.

In other embodiments different components and configurations thereof are used to form a resonant circuit 108 having a resonant frequency at which the resonant circuit 108 is energized and emits a signal. Additionally, various values and combinations of capacitance 110 and inductance 112 can be used. Moreover, the resonant circuit 108 may include various components known in the art to emit corresponding signals such as audio or radio frequency waves when the circuit 108 is energized. Furthermore, the circuit 108 may not include any component to specifically emit a light signal and instead utilize an electromagnetic field or heat as a signal which are both generated when the circuit 108 is energized.

FIG. 2A is a front perspective view illustrating the positioning tray 116 with the plurality of caps 100 arranged therein according to one embodiment of the invention. The positioning tray 116 has a plurality of positions 118, each position 118 for receiving one of the plurality of caps 100. The illustrated positioning tray 116 is designed to receive cylindrically shaped caps 100 because the rotational symmetry of the caps 100 allows each position 118 to receive caps 100 despite rotation around the z-axis with respect to the position 118. However, each position 118 can be altered to correspond to the size and shape of each of the plurality of caps 100. Accordingly, the size and shape of the positioning tray 116 can be altered to correspond to each of the plurality of positions 118 and the size and shape of each of the plurality of caps 100.

Figure 2B:
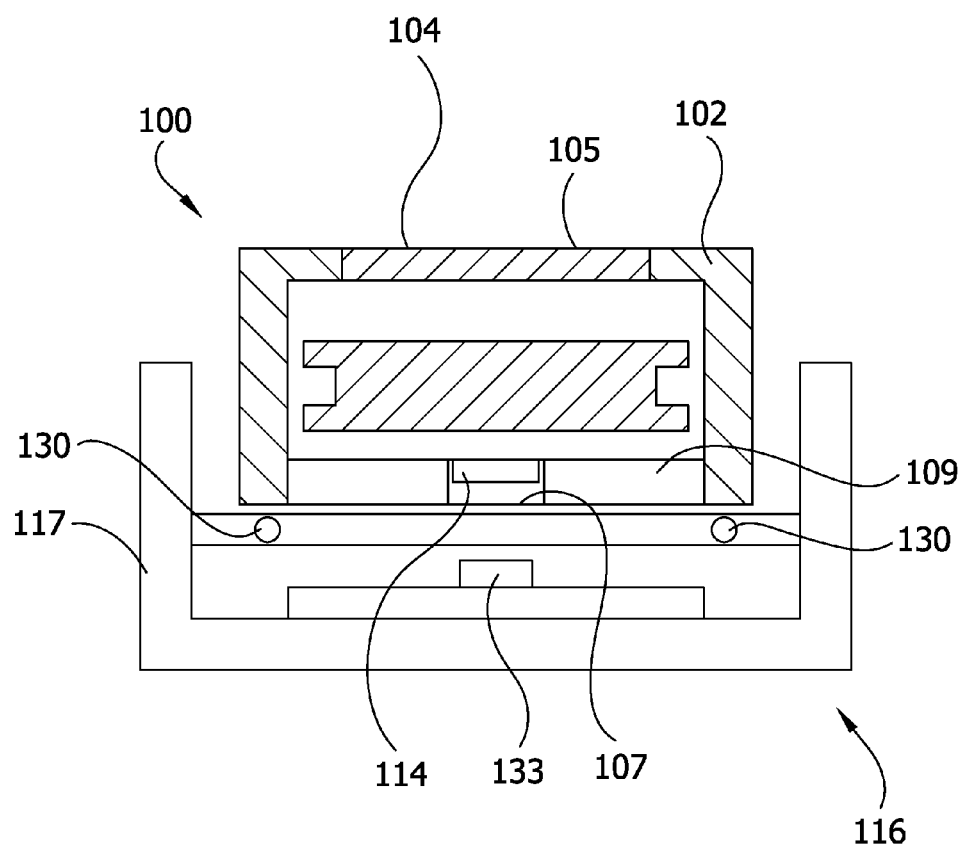
FIG. 2B is a side, orthogonal, cross-sectional view illustrating the positioning tray with a cap arranged therein according to one embodiment of the invention.

The positioning tray 116 further includes the energizing circuit 130 that energizes each of the unique circuits 108 of the caps 100. In one embodiment, the energizing circuit 130 comprises a wire loop as shown in FIG. 2B. In other embodiments, the loop comprises various conductive materials known in the art. In one embodiment, the positioning tray 116 includes a protective outer casing 117 within which the energizing circuit is encased. In other embodiments, the energizing circuit is embedded on a surface of the positioning tray 116.

The positioning tray 116 further includes detectors 133 for emitting a detection signal for indicating the position 118 of each of the caps 100 by detecting the signal emitted by each of the plurality of caps 100. In one embodiment, as shown in FIG. 3, the detector comprises a matrix 132 having a plurality of individual detectors 133, each individual detector located at one particular position 118 on the positioning tray 116. In one embodiment, the individual detectors each comprise a photodetector. Each photodetector 133 comprises an individual phototransistor 134 located at one position 118 on the positioning tray 116 such that when the LED 114 in a cap 100 arranged in the particular position 118 illuminates, it is detected by the phototransistor 134 located at the particular position 118. In alternate embodiments, various detectors known in the art are located in various configurations on the positioning tray 116 and emit a detection signal for indicating the position 118 of each of the plurality of caps 100 by detecting the signal emitted by each of the plurality of caps 100.

In the embodiment illustrated in FIG. 3, after the subject undergoing color discrimination testing arranges the plurality of the caps 100 in the positioning tray 116 according to how the subject perceives the displayed color 104, a user can initiate computation of results of the testing using a computing device. In other embodiments, other input devices known in the art capable of initiating controller operation are used.

The computing device transmits a signal, through a universal serial bus interface 122, initiating the determination of the positions 118 of each cap 100 to a microcontroller 120. When the microcontroller 120 receives the signal, it controls the energizing circuit 130. In one embodiment, the microcontroller 120 is an 8 bit flash microcontroller PIC16F84A. In alternate embodiments, various other types of controllers known in the art, such as a programmable logic controller are used. Additionally in alternate embodiments, various other links, including wireless technologies, are used transmit data between the input device and the controller.

The microcontroller 120 initiates the energizing circuit 130 by providing a digital signal to a digital to analog converter (D/A) 124. The D/A 124 converts the digital signal provided by the microcontroller 120 to an analog voltage signal. A voltage controlled oscillator (VCO) 126 uses the analog voltage signal to generate an oscillating signal. The oscillating signal has a frequency determined by the analog voltage signal. An amplifier 128 amplifies the oscillating signal producing an amplified sinusoidal signal and outputs the amplified oscillating signal to the wire loop 130 in the positioning tray 116. In alternate embodiments wherein various other energizing circuits known in the art are located in the positioning tray 116, various corresponding signals that powers the energizing circuit known in the art are outputted from the controller.

The wire loop 130 conducts the amplified oscillating signal generating an electromagnetic field oscillating at a frequency corresponding to the frequency of the amplified oscillating signal. When the frequency of the electromagnetic field is substantially the same as the resonant frequency of the passive resonant circuit 108 in one of the plurality of the caps 100, energy is absorbed by the resonant circuit 108 generating a current in the resonant circuit 108. The current in the resonant circuit 108 causes the LED 114 to illuminate. In alternate embodiments the energizing circuit generates other signals known in the art which energize each of the unique circuits of the plurality of caps 100.

Figure 4:
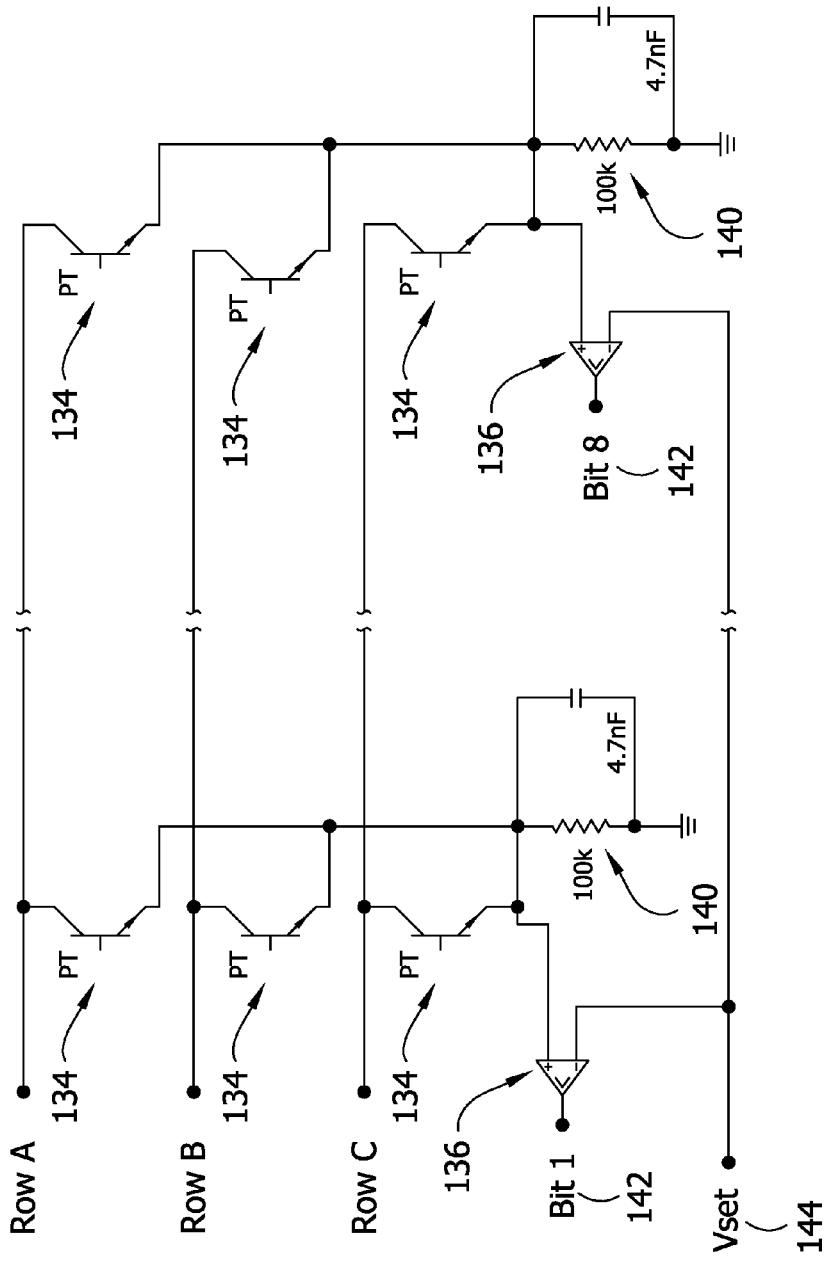
FIG. 4 is a circuit schematic of the photodetector matrix and comparator components according to one embodiment of the invention.

FIGS. 3 and 4 illustrate the photodetector matrix 132 and comparator 136 components according to one embodiment of the invention. The phototransistors 134 are powered using buses 138. Each bus 138 supports up to 8 phototransistors 134. Although other power configurations can be used, this power configuration is used so that each bus 138 can be represented by a byte with each phototransistor 134 represented by a corresponding bit 142. Byte A contains the bits 142 representing the phototransistors 134 located in the first eight (1-8) positions 118 in the positioning tray 116. Byte B contains the bits 142 representing the phototransistors 134 located in the next eight (9-16) positions 118 in the positioning tray 116. Byte C contains the bits 142 representing the phototransistors 134 located in the last remaining six (17-22) positions 118 in the positioning tray 116. When a phototransistor 134 receives power and detects light from an illuminated LED 114, the phototransistor 134 allows current to flow through it. The current then flows through a resistor 140 creating a voltage. A comparator 136 compares the voltage developed across the resistor 140 with a threshold voltage 144 selected to prevent false detections of light. The comparator 136 sets the bit 142 corresponding to the phototransistor 134 where the voltage developed across the resistor 140 is greater than the threshold voltage 144. The set bit 142 indicates the position where the subject arranged the cap 100 having the illuminated LED 114 since the bit 142 will only be set when a phototransistor 134 at a particular position 118 detects light.

Each time the microcontroller 120 initiates energizing the loop in the positioning tray, the microcontroller 120 sends a digital signal to a microcontroller 146 to read and send bytes A, B, and C, indicating the position 118 of a particular detected cap 100. Microcontroller 146 sends the read Bytes A, B, and C to the microcontroller 120 using a synchronous 2 wire data/clock protocol. In one embodiment the microcontroller 146 is an 8 bit flash PIC16F84. In alternate embodiments, various other types of controllers known in the art, such as a programmable logic controller, are used. Microcontroller 120 records and sends to the computing device the detected position of the particular cap 100 where the position 118 has not previously been detected. The universal serial bus 122 links the microcontroller 120 to the computing device for transferring the recorded position of the plurality of caps 100 to the computing device. The computing device uses the recorded position of the plurality of caps 100 to compute the color discrimination of the subject.

Figure 5:
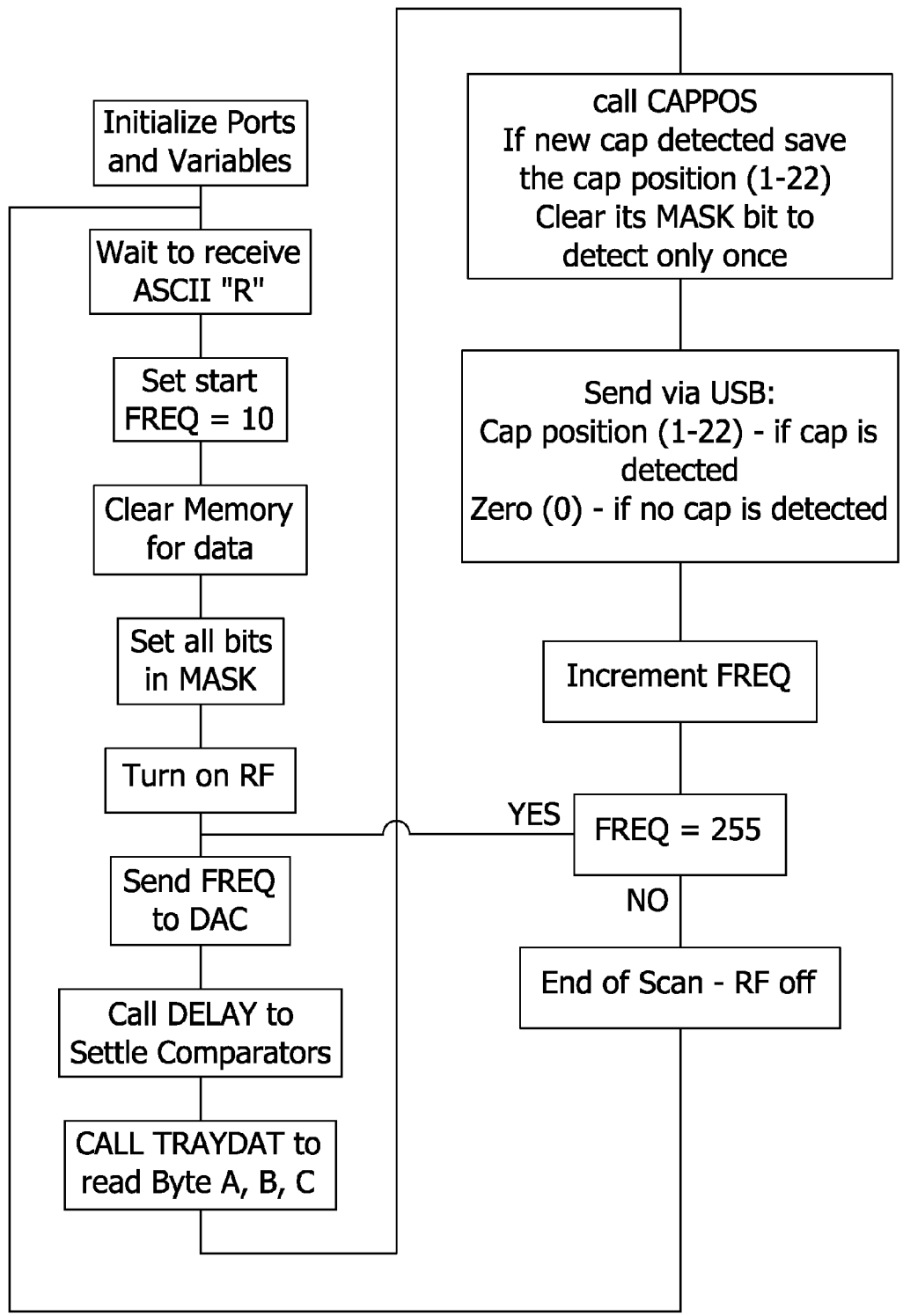
FIG. 5 is an exemplary flow diagram illustrating the operation of one software program for controlling an energizing loop according to one embodiment of the invention.

FIG. 5 is an exemplary flow diagram illustrating the operation of one software program for controlling an energizing loop according to one embodiment of the invention. This first software program is run from the microcontroller 120. When a user indicates to the input device his desire to obtain the results of the test, the input device sends an ASCII "R" character to the microcontroller 120. The microcontroller 120 uses the first software program to scan a radio frequency range in discrete steps. Each frequency corresponds to a digital number (10-255). The digital number (10-255) is provided by the microcontroller 120 to the DAC 124. At each frequency, microcontroller 120 signals microcontroller 146 to call a second software program.

Figure 6:
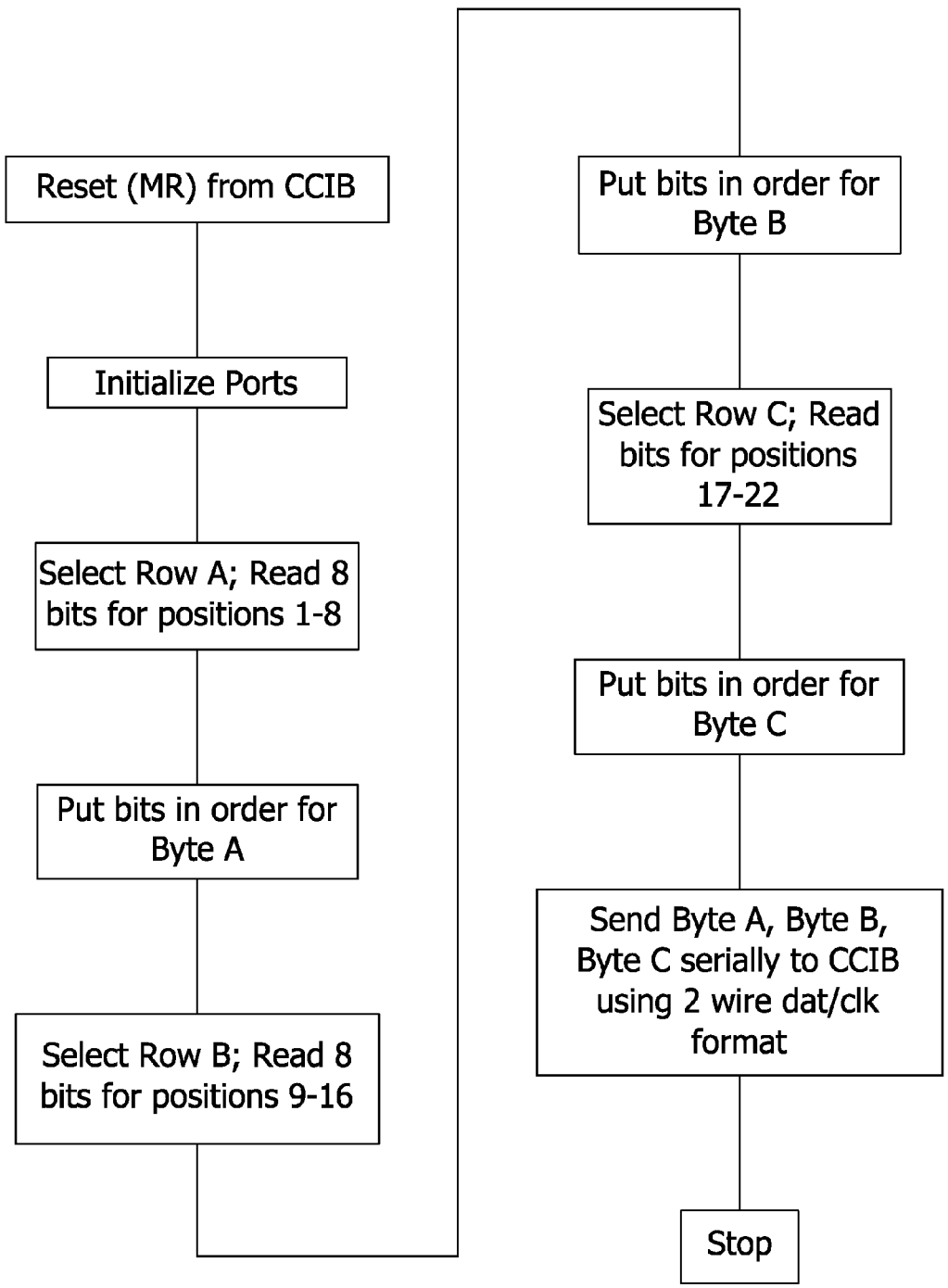
FIG. 6 is an exemplary flow diagram illustrating the operation of a second software program for detecting signals from the photodetector matrix of FIG. 3 according to one embodiment of the invention.

FIG. 6 is an exemplary flow diagram illustrating the operation of the second software program to poll each of the plurality of caps 100 to detect resonance, at the frequency initiated by the first software program, as indicated by an illuminated LED 114 and detected by the corresponding phototransistor 134. After initializing ports, the second software program outputs a signal to power each bus 138 sequentially. When a particular bus 138 is powered, the software program reads the bits 142 comprising the byte A, B, or C corresponding to the particular bus 138. After each of the buses have been powered and bytes A, B, and C have been read, the second software program sends the bytes A, B, and C to the microcontroller 120.

The microcontroller 120 determines whether the position indicated by bytes A, B, and C has previously been detected and records the position where the position has not previously been detected. The microcontroller 120 then sends the recorded position to the computing device. The process is repeated for each of the 245 frequencies applied to the energizing circuit 130. For each of the 245 frequencies, a single number is sent to the computing device. For frequencies that have a cap 100 in resonance and the position 118 of the cap has not previously been detected, the number sent is the binary number of the position 118 corresponding to the cap 100 in resonance. For frequencies that do not have a cap 100 in resonance or the position 118 of the cap 100 in resonance has previously been detected, the number sent is the binary number zero. Accordingly, when the process is complete for each of the 245 frequencies applied to the energizing circuit 130, the computing device will have a sequence of 245 binary numbers with 22 of them non-zero. The computing device removes the zeros to yield a sequence of cap positions. Each cap position in the sequence represents the position of the corresponding cap where the caps are arranged in ascending order of resonant frequency. The computing device then uses the positions to automatically score the subject's cap arrangement test. The score can be compared with scores and other information stored by the computing device to provide the subject with additional information related to the score. For example, the additional information could indicate the subject's level of color discrimination and provide a tentative diagnosis.

The software logic of the first and second software programs provides for a particularly accurate determination of cap position. The frequencies applied to the energizing circuit which are used to energize the caps are applied in an ascending order such that the $n^{th}$ cap will always have a resonance before the $n^{th+1}$ cap. Once a cap position is detected, it is recorded. The recorded position is compared to subsequently detected cap positions to prevent a particular cap position from being recorded more than once. Thus, each cap 100 is detected in the proper order and the corresponding position 118 is recorded only once. Accordingly, all that is required for an accurate determination of cap positions is to monotonically apply the frequencies of each of the cap resonances to the plurality of caps. This feature makes the invention more robust to variability in the cap resonant components as well as the precise frequency of the energizing circuit. In alternative embodiments, other software logic known in the art is used to control the energizing loop, detect signals from the photodetector matrix 132, and communicate the detected position to the computing device.

Additionally, in alternative embodiments, other features which avoid detecting and recording a cap more than once are included to provide for an accurate determination of cap position. According to one feature, the frequency intervals corresponding to the frequencies generated by the electromagnetic field are selected such that each frequency generated by the electromagnetic field is substantially the same as only one resonant frequency. Thus, the frequencies generated by the electromagnetic field energize only one cap at a time. The frequency intervals can be selected using the discrete step included in the first software program. According to another feature, the resonant frequencies of each cap are separated by frequency intervals wherein the frequency intervals are selected such that only one cap can be energized at a particular frequency generated by the electric field. The frequency intervals can be selected according to the relationship between the resonant frequency and the electrical components of the resonant circuit of each cap.

Having described the invention in detail, it will be apparent that modifications and variations are possible without departing from the scope of the invention defined in the appended claims.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A device for determining color discrimination of a subject, the device comprising:
   a plurality of caps, each displaying a different hue, each said cap having a unique circuit which emits a response signal when energized by an energization signal corresponding to said unique circuit, each said unique circuit of a particular cap associated with said color of the particular cap, and the energization signal corresponding each unique circuit is different from the energization signal corresponding to each other unique circuit;
   a positioning tray having a plurality of positions, each position for receiving each one of the plurality of caps;
   an energizing circuit coupled to the positioning tray for individually generating the energization signal corresponding to each of the unique circuits for energizing the unique circuits of the plurality of caps;
   a detector coupled to the positioning tray for detecting whether a response signal has been emitted, and generating a detection signal for indicating the position of each of the plurality of caps based on said detecting; and
   a controller connected to the detector for recording the detected position of each energized cap wherein when the subject places the caps in positions of the tray according to their colors and when each cap is energized by energizing circuit, then the position of each cap in the positioning tray is indicated and recorded to indicate the color discrimination of the subject.

2. The device according to claim 1, further comprising a converter for converting the detection signal generated by the detector to a digital detection signal for use by the controller to record the detected position of each energized cap.

3. The device according to claim 2, wherein said converter includes a comparator, said comparator comparing the detection signal generated by the detector with a minimum signal and for providing the digital detection signal to the controller when the comparator indicates that the detection signal equals or exceeds the minimum value.

4. The device according to claim 1, further comprising a link for transferring the recorded position of the plurality of caps from the controller to a computing device using the recorded position of the plurality of caps to automatically compute the color discrimination of the subject.

5. The device according to claim 1, wherein the detector comprises a matrix having a plurality of subject detectors, each said subject detector located at one particular position for detecting the response signal emitted by the cap at the particular position when the cap is energized.

6. The device according to claim 5, wherein said subject detectors each comprise a photodetector.

7. The device according to claim 1, wherein the controller prevents the detected position from being recorded more than once.

8. The device according to claim 1, wherein each said unique circuit is a passive resonant circuit having a unique resonant frequency.

9. The device according to claim 8, wherein said controller controls the energizing circuit to selectively energize each of the passive resonant circuits in an ascending order based on the resonant frequency of each of the passive resonant circuits.

10. The device according to claim 8, wherein said energizing circuit is a loop for conducting a signal oscillating at selected frequencies generating an electromagnetic field oscillating at the unique resonant frequency of each of the passive resonant circuits.

11. The device according to claim 8, wherein said passive resonant circuit includes a capacitance and an inductance electrically connected in parallel, said inductance being substantially the same for each of the plurality of caps and said capacitance being different for each of the plurality of caps.

12. The device according to claim 1, wherein each said unique circuit contains a light emitting diode and said signal is light emitted from said light emitting diode.

13. The device according to claim 1, wherein said controller controls the energizing circuit to energize selectively the circuits in each of the plurality of caps.

14. The device according to claim 13, wherein said controller includes a first microcontroller and a second microcontroller, said first microcontroller for controlling the energizing circuit to energize selectively the unique circuits in each of the plurality of caps, said second microcontroller connected to the detector for reading the detected position of each energized cap, said first microcontroller for recording the detected position read by the first microcontroller.

15. A method for obtaining data to determine color discrimination of a subject by determining the position of a plurality of uniquely colored caps arranged by a subject, said method comprising:
   transmitting an electronic signal to energize selectively a unique circuit in each of the plurality of uniquely colored caps;

detecting a response signal when the unique circuit contained in each of the uniquely colored caps is energized; and determining the position of each of the plurality of uniquely colored caps after placement by said subject based upon detecting the response signal and thereby obtaining data to determine color discrimination of the subject.

16. The method according to claim 15, said transmitting comprises generating an oscillating signal with a varying frequency.

17. The method according to claim 15, further comprising transferring the determined position of each of the plurality of uniquely colored caps to a computing device to determine the color discrimination of the subject.

18. The method according to claim 17, wherein the response signal is an emission of light.

19. The method according to claim 18, wherein the circuit contained in each of the plurality of uniquely colored caps has a unique resonant frequency.

20. The method according to claim 19, wherein the circuit contained in each of the plurality of uniquely colored caps is energized at the unique resonant frequency of said circuit.

* * * * *